United States Patent [19]
Remans et al.

[11] Patent Number: 5,811,601
[45] Date of Patent: Sep. 22, 1998

[54] ISOMERIZATION OF VINYL GLYCOLS TO UNSATURATED DIOLS

[75] Inventors: Thomas J. Remans, Hasselt; Pierre A. Jacobs, Gooik; Johan Martens, Huldenberg, all of Belgium; Dominicus A. G. van Oeffelen; Mathias H. G. Steijns, both of Terneuzen, Belgium

[73] Assignee: The Dow Chemical Company, Midland, Mich.

[21] Appl. No.: 689,428

[22] Filed: Aug. 9, 1996

[51] Int. Cl.$^6$ .................... C07C 33/025; C07C 33/03; C07C 31/20
[52] U.S. Cl. ............................... 568/857; 502/60
[58] Field of Search ................ 568/857; 502/60

[56] References Cited

U.S. PATENT DOCUMENTS

| | | | |
|---|---|---|---|
| 2,911,445 | 11/1959 | Friederich | 260/635 |
| 5,117,012 | 5/1992 | Stavinoha, Jr. et al. | 549/538 |
| 5,166,372 | 11/1992 | Crocco et al. | 549/531 |
| 5,336,815 | 8/1994 | Becker | 568/857 |

FOREIGN PATENT DOCUMENTS

| | | |
|---|---|---|
| 0 190 609 | 1/1990 | European Pat. Off. . |
| 2 734 240 | 2/1979 | Germany . |
| 4 342 030 | 6/1994 | Germany . |
| 4 429 699 | 3/1995 | Germany . |
| 4 429 700 | 3/1995 | Germany . |
| 57 002 227 | 7/1982 | Japan . |

OTHER PUBLICATIONS

WPAT abstract of J59 084 831;, 1984.
WPAT abstract of JP 54–073710, 1979.
WPAT abstract of JP 53–127405, 1978.
WPAT abract of 62–054788, 1987.
WPAT abstract of DE 7743846, 1979.
WPAT abstract of JP 49–049910, 1974.

*Primary Examiner*—Ceila Chang
*Assistant Examiner*—D. Margaret M. Mach

[57] ABSTRACT

This invention relates to a process for the isomerization of a vinyl glycol to an unsaturated diol in the presence of a rhenium-based catalyst; and to a catalyst for said isomerization. More specifically, this invention relates to the isomerization of 3-butene-1,2-diol to 2-butene-1,4-diol; and to a process for the manufacture of 1,4-butanediol involving the step of isomerizing 3-butene-1,2-diol to 2-butene-1,4-diol in the presence of said catalyst. The catalyst is characterized in that it comprises a transition metal on a carrier wherein the carrier is a zeolite Y type substance containing silicon and aluminum in a mole ratio of from about 1.5:1 to about 1000:1, and the transition metal is rhenium or a rhenium compound and mixtures thereof present in an amount of from about 0.1 to about 50 weight percent based on total combined weight of the carrier and of the rhenium or rhenium compound and mixtures thereof.

10 Claims, No Drawings

ISOMERIZATION OF VINYL GLYCOLS TO UNSATURATED DIOLS

BACKGROUND OF THE INVENTION

This invention relates to a process for the isomerization of a vinyl glycol to an unsaturated diol. It is known that certain unsaturated alcohols when heated or subjected to acidic or basic conditions undergo an isomerization identified as an allyl rearrangement in which the migration of a hydroxyl group in a beta-position takes place with the displacement of the carbon-carbon double bond. Substances known to promote such an isomerization include water-soluble mercuric salts employed under acidic conditions such as disclosed in U.S. Pat. No. 2,911,445; metal iodides such as disclosed in JP 59-084,831 and JP 82-002,227; and calcium compounds such as disclosed in JP 79-073,710.

To date such rearrangement reactions of unsaturated alcohols have not found prominent use in industrial processes due to poor selectivity and/or poor yield. It would therefore be desirable to provide for a reaction procedure using a catalyst which is able to provide for a greater selectivity and preferably in combination with an enhanced yield.

A substance of prime industrial importance is 1,4-butanediol which can be obtained by the hydrogenation of 2-butene-1,4-diol. Accordingly, it would be desirable to develop a process for the manufacture of 1,4-butanediol employing the rearrangement reaction of an unsaturated alcohol to provide, as intermediate, 2-butene-1,4-diol. 1,4-Butanediol is an important industrial commodity of value in the polymer industry and in the pharmaceutical industry.

SUMMARY OF THE INVENTION

In a first aspect, this invention relates to a process for the isomerization of a vinyl glycol of the general formula

$$HO-CHR-CHOH-CH=CR'H \quad (I)$$

wherein R and R' independently represent hydrogen or a lower alkyl to an unsaturated diol of the general formula

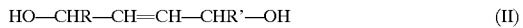

$$HO-CHR-CH=CH-CHR'-OH \quad (II)$$

wherein R and R' independently represent hydrogen or a lower alkyl which comprises contacting the vinyl glycol with rhenium, a rhenium compound and mixtures thereof.

In a second aspect, this invention relates to a process for the preparation of 2-butene-1,4-diol by isomerization of 3-butene-1,2-diol in the presence of a supported transition metal catalyst characterized in that the catalyst is selected from the group consisting of rhenium, a rhenium compound and mixtures thereof and is supported by a zeolite type carrier comprising silicon and aluminum in an atom ratio of from about 1:1 to about 1000:1.

In a third aspect, this invention relates to a process for the preparation of 1,4-butanediol comprising the step of isomerizing 3-butene-1,2-diol to 2-butene-1,4-diol in the presence of a supported transition metal catalyst characterized in that the catalyst is selected from the group consisting of rhenium, a rhenium compound and mixtures thereof and is supported by a zeolite type carrier comprising silicon and aluminum in an atom ratio of from about 1:1 to about 1000:1.

In a fourth aspect, this invention relates to a catalyst, suitable for the conversion of a vinyl glycol to an unsaturated diol, which comprises a transition metal on a carrier characterized in that: the carrier is a faujasite type zeolite which contains silicon and aluminum in an atom ratio of from about 1:1 to about 1000:1; and in that the transition metal is rhenium or a rhenium compound and mixtures thereof present in an amount of from about 0.1 to about 50 weight percent based on total combined weight of the carrier and of the rhenium or rhenium compound and mixtures thereof.

Applicants have found that such rhenium-based catalyst are able to promote the rearrangement of vinyl glycols to unsaturated diols at a surprisingly high selectivity.

DETAILED DESCRIPTION OF THE INVENTION

According to the present invention, the isomerization of a vinyl glycol to the unsaturated diol is carried out in the presence of a supported transition metal catalyst. The transition metal of preference is rhenium present as rhenium metal, a rhenium compound and mixtures thereof, preferably supported by a silica-based carrier. Advantageously, the supported catalyst consists substantially of rhenium metal, or a rhenium compound. Based on the combined total weight of the carrier and transition metal, the rhenium or rhenium compound is present in an amount of from 0.1 to about 50, preferably from about 1 to about 30, and more preferably from about 5 to about 25, and yet more preferably from about 8 to about 20 weight percent.

The support, or carrier, is a silica-based substance having a structure recognized as being a faujasite type zeolite, which comprises silicon and aluminum in an atom ratio of from about 1:1 to about 1000:1 preferably a Y type zeolite with a silicon and aluminum ratio of 1.5:1 to about 200:1, and more preferably an ultra-stabilized faujasite type zeolite with a Si/Al ratio of from about 5:1 to about 100:1. Exemplary of suitable carriers include zeolites such as the product CBV-780 available from Pennsylvania Quartz Corporation and understood to be a Y type zeolite with a Si/Al ratio of about 40:1.

The support can be loaded with the rhenium or rhenium compound by any method generally employed for the loading of such supports. Such methods include bringing the support into contact with an aqueous metal salt solution, subsequently drying the support and optionally calcining. For the present disclosure, suitable metal salts include water soluble rhenium-containing substances including $HReO_4$, $KReO_4$, $NaReO_4$ and other $ReO_4$ salts, $ReCl_5$, $ReCl_4$, $ReCl_3$, $ReF_6$, $Re_2O_7$ and preferably $NH_4ReO_4$.

The above described supported catalyst is found to be of particular value for promoting the rearrangement of a vinyl glycol to an unsaturated diol. The vinyl glycols include substances of the following general formula

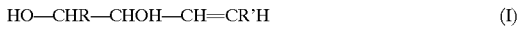

$$HO-CHR-CHOH-CH=CR'H \quad (I)$$

wherein R and R' independently represent hydrogen or a lower alkyl. By lower alkyl it is understood moieties containing from 1 to 6 carbon atoms. R and R' can also be a part of an alicyclic structure. For the present invention the preferred vinyl glycol is where both R and R' is hydrogen, as exemplified by 3-butene-1,2-diol.

The unsaturated diols obtained according to this invention are characterized by the following general formula

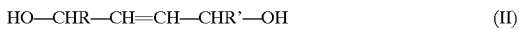

$$HO-CHR-CH=CH-CHR'-OH \quad (II)$$

wherein R and R' independently represent hydrogen or a lower alkyl and as described for the vinyl glycol. When the starting vinyl glycol is 3-butene-1,2-diol, the resulting diol is 2-butene-1,4-diol.

As mentioned above, one aspect of this invention is to provide a procedure for the manufacture of 1,4-butanediol employing an intermediate step of isomerizing 3-butene-1, 2-diol to 2-butene-1,4-diol. The following reaction scheme illustrates a procedure for the manufacture of 1,4-butanediol starting from 1,3-butadiene, a widely available industrial feedstock, and involving the discussed isomerization reaction:

Step 1: Conversion of 1,3-butadiene to 1,2-epoxy-3-butene;

Step 2: Hydrolysis of 1,2-epoxy-3-butene to 3-butene-1, 2-diol;

Step 3: Isomerization of 3-butene-1,2-diol to 2-butene-1, 4-diol;

Step 4: Hydrogenation of 2-butene-1,4-diol to 1,4-butanediol.

For Step 1, 1,3-butadiene can be converted to 1,2-epoxy-3-butene by an appropriate epoxidizing agent. Such agents include hydrogen peroxide in the presence of an acid catalyst such as disclosed in DE 2,734,240; oxygen in the presence of a silver catalyst such as disclosed in U.S. Pat. No. 5,117,012; hydrogen peroxide/alcohol/water mixtures in the presence of an organorhenium catalyst such as disclosed in U.S. Pat. No. 5,166,372; hydrogen peroxide in the presence of Ti/Si catalysts as disclosed in European Patent 190,609.

For Step 2, 1,2-epoxy-3-butene can be hydrolyzed to obtain 3-butene-1,2-diol by an appropriate hydrolyzing agent. Such agents and procedures include acid catalyzed solvolysis such as disclosed in the publication Tetrahedron Asymmetry page 15–16, Vol. 6, 1995; water as disclosed in DE 4,342,030; water in the presence of $SiO_2/TiO_2/F$ as disclosed in DE 4,429,699; water in the presence of rhenium oxide ($Re_2O_7$) as disclosed in DE 4,429,700.

For Step 3; isomerization of 3-butene-1,2-diol to 2-butene-1,4-diol in the presence of the supported rhenium catalyst as described above.

For Step 4; 2-butene-1,4-diol can be hydrogenated by procedures employing hydrogen over nickel catalysts such as disclosed in JP 53-127,405; JP 62-054,788; JP 74-049,910; JP 79-061,108.

The preparation of 1,4-butanediol is presented as a four step procedure, however a person skilled in the art of organic synthesis will be aware that Steps 1 and 2 can be combined.

The following examples are presented to illustrate the invention. Unless otherwise specified all amounts are given in parts by weight.

Preparation of Catalyst 1

A rhenium-containing catalyst is prepared by mixing 60 parts of an ultrastable Zeolite Y carrier US-Y CBV-780, available from the Pennsylvania Quartz Corp. and having a Si/Al ratio of 40:1, with 8.6 parts of $NH_4ReO_4$ dissolved in 60 parts of water at 40° C. The resulting slurry is then placed in an oven and dried by progressively increasing the temperature at the rate of 1° C./min from 20° C. to 100° C. and subsequently maintaining it at 100° C. for about one hour. The oven temperature is then increased at a rate of 3° C./min to 250° C. and the dried slurry calcined for a period of 5 hours. The resulting catalyst contains 10 weight percent Re(VII)oxide.

Preparation of Catalysts 2, 3 and 4

Additional catalysts are prepared according to the same general procedure as given for Catalyst 1.
Catalyst 2 contains 1 weight percent Re(VII) oxide on the ultrastable Zeolite Y carrier US-Y CBV-780.
Catalyst 3 contains 5 weight percent Re(VII) oxide on the ultrastable Zeolite Y carrier US-Y CBV-780.
Catalyst 4 contains 30 weight percent Re(VII) oxide on the ultrastable Zeolite Y carrier US-Y CBV-780.

Comparative Catalysts 5, 6 and 7

Catalyst 5 is ultrastable Zeolite Y carrier US-Y CBV-780 in absence of a rhenium substance.
Catalyst 6 is $Re_2O_7$ of 99.9% purity as available from Aldrich.
Catalyst 7 is $\gamma$-$Al_2O_3$ with a surface area of 316 $m^2/g$ as available from Rhône-Poulenc loaded with 10 weight percent Rhenium; prepared according to the general procedure as mentioned for Catalyst 1.

Isomerization of 3-butene-1,2-diol to 2-butene-1,4-diol

Catalysts 1 to 4 are used to effect the conversion of 3 butene-1,2-diol to 2-butene-1,4-diol according to the following general procedure.

3-Butene-1,2-diol is obtained by the hydrolysis of 1,2-epoxy-3-butene (0.75 parts, purity 99%) in water (37.5 parts) at 100° C.; the resulting mixture according to GC analysis, on a CP-Sil-5-column, contained 90 mole percent of 3-butene-1,2-diol, 8 mole percent of 2-butene-1,4-diol, and 2 mole percent of 2-butenal. The obtained 3-butene-1, 2-diol mixture is brought into contact with 0.1 parts of the catalyst and heated to 150° C. for an extended period of time. The isomerization of 3-butene-1,2-diol to 2-butene-1, 4-diol is followed by determining the composition of the mixture using GC analysis after 1, 3 and 5 hours. Table 1 presents the extent of mole conversion and the degree of selectivity exhibited by the catalysts.

TABLE I

| | | 1 hour | 3 hours | 5 hours |
|---|---|---|---|---|
| Catalyst 1 (10 wt. % Re) | Conversion (mole %) Selectivity: (%) | 1.5 | 2.0 | 5.5 |
| | 2-butene-1,4-diol | 88.2 | 87 | 86.9 |
| | 2-butenal | 0.8 | 0.6 | 3.9 |
| | 3-butenal | 0 | 0 | 0 |
| Catalyst 2 (1 wt. % Re) | Conversion (mole %) Selectivity: (%) | 0.8 | 2.8 | 3.1 |
| | 2-butene-1,4-diol | 64.3 | 52.5 | 0 |
| | 2-butenal | 35.6 | 47.5 | 68.8 |
| | 3-butenal | 0 | 0 | 0 |
| Catalyst 3 (5 wt. % Re) | Conversion (mole %) Selectivity: (%) | 1.2 | 2.0 | 3.1 |
| | 2-butene-1,4-diol | 60.6 | 55.1 | 49.3 |
| | 2-butenal | 38.0 | 45.0 | 50.7 |
| | 3-butenal | 0 | 0 | 0 |
| Catalyst 4 (30 wt. % Re) | Conversion (mole %) Selectivity: (%) | 0.2 | 3.9 | 10.0 |
| | 2-butene-1,4-diol | 0 | 0 | 0 |
| | 2-butenal | 50.8 | 0 | 0 |
| | 3-butenal | 0 | 0 | 0 |

The results presented in Table I show the ability of the rhenium based catalyst to isomerize a vinyl glycol to an unsaturated diol with a large degree of selectivity. The extent of selectivity is dependent on the amount of rhenium present on the catalyst. The optimum amount of Rhenium required to be present is dependent on the vinyl glycol to be isomerized and needs to be established by routine experimentation.

Comparative Examples

As comparative examples, the rearrangement of 3-butene-1,2-diol is performed in the presence of 0.1 part unsupported Re$_2$O$_7$; 0.1 part of US-Y Si/Al=40; and 0.1 part of a catalyst containing 10 weight percent Re on a γ-Al$_2$O$_3$ prepared as stated above for Catalyst 1. The results given in Table II illustrate the low selectivity for 2-butene-1,4-diol obtained in the presence of these catalysts.

TABLE II

|  |  | 1 hour | 3 hours | 5 hours |
|---|---|---|---|---|
| Catalyst 5 | Conversion (mole %) | 0.2 | 0.5 | 1.0 |
|  | Selectivity: (%) |  |  |  |
|  | 2-butene-1,4-diol | 1.6 | 1.4 | 1.3 |
|  | 2-butenal | 95.4 | 95.6 | 85 |
|  | 3-butenal | 0 | 0 | 0 |
| Catalyst 6 | Conversion (mole %) | 6.1 | 19.3 | 41.7 |
|  | Selectivity: (%) |  |  |  |
|  | 2-butene-1,4-diol | 0 | 0 | 0 |
|  | 2-butenal | 34.7 | 40.3 | 48.9 |
|  | 3-butenal | 0 | 0 | 0 |
| Catalyst 7 (10 wt. % Re on γ-Al$_2$O$_3$) | Conversion (mole %) | 6 | 8 | 16 |
|  | Selectivity: (%) |  |  |  |
|  | 2-butene-1,4-diol | 52 | 10 | 0 |
|  | 2-butenal | 42 | 65 | 86 |
|  | 3-butenal | 0 | 0 | 0 |

What is claimed is:

1. A process for the isomerization of a vinyl glycol of the general formula

HO—CHR—CH.OH—CH=CR'H　　(I)

wherein R and R' independently represent hydrogen or a lower alkyl to an unsaturated diol of the general formula

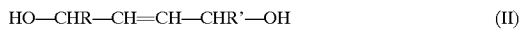

HO—CHR—CH=CH—CHR'—OH　　(II)

wherein R and R' independently represent hydrogen or a lower alkyl which comprises contacting the vinyl glycol with a substance consisting of rhenium, a rhenium compound and mixtures thereof and the rhenium, a rhenium compound and mixtures thereof is supported by a silica-based carrier.

2. The process of claim 1 wherein the silica-based carrier is a zeolite.

3. The process of claim 2 wherein the zeolite is a faujasite type substance.

4. The process of claim 3 wherein the carrier comprises silicon and aluminum in an atom ratio of from about 1:1 to about 1000:1.

5. The process of claim 4 wherein the carrier comprises silicon and aluminum in an atom ratio of from about 1.5:1 to about 100:1.

6. The process of claim 2 wherein the rhenium or rhenium compound and mixtures thereof is present in an amount of from about 0.1 to about 50 weight percent based on total combined weight of the carrier and of the rhenium or rhenium compound and mixtures thereof.

7. The process of claim 6 wherein the rhenium or rhenium compound and mixtures thereof is present in an amount of from about 1 to about 30 weight percent.

8. The process of claim 7 wherein the rhenium or rhenium compound and mixtures thereof is present in an amount of from about 5 to about 25 weight percent.

9. A process for the preparation of 2-butene-1,4-diol by isomerization of 3-butene-1,2-diol in the presence of a supported transition metal catalyst characterized in that the catalyst is selected from the group consisting of rhenium, a rhenium compound and mixtures thereof and is supported by a faujasite type zeolite carrier comprising silicon and aluminum in an atom ratio of from about 1.5:1 to about 1000:1.

10. A process for the preparation of 1,4-butanediol comprising the intermediate step of isomerizing 3-butene-1,2-diol to 2-butene-1,4-diol in the presence of a supported transition metal catalyst characterized in that the transition metal is selected from the group consisting of rhenium, a rhenium compound and mixtures thereof, and is supported by a zeolite Y type carrier comprising silicon and aluminum in an atom ratio of from about 1.5:1 to about 1000:1.

* * * * *